United States Patent
Tao

(10) Patent No.: US 6,383,524 B2
(45) Date of Patent: May 7, 2002

(54) COMPOSITIONS AND METHODS FOR ENHANCING THERAPEUTIC EFFECTS

(75) Inventor: Yuanjin Tao, Fremont, CA (US)

(73) Assignee: TheraLife, Inc., Los Altos, CA (US)

( * ) Notice: Subject to any disclaimer, the term of this patent is extended or adjusted under 35 U.S.C. 154(b) by 0 days.

(21) Appl. No.: 09/872,082

(22) Filed: Jun. 1, 2001

Related U.S. Application Data

(60) Provisional application No. 60/208,990, filed on Jun. 1, 2000.

(51) Int. Cl.⁷ .............................................. A61K 35/78
(52) U.S. Cl. ................. 424/725; 424/728; 424/757; 514/458; 514/460; 514/461; 514/558
(58) Field of Search ............................. 424/725, 728, 424/757; 514/458, 560, 561, 558

(56) References Cited

U.S. PATENT DOCUMENTS

| | | | |
|---|---|---|---|
| 5,118,505 A | 6/1992 | Költringer | 424/752 |
| 5,149,521 A | 9/1992 | Hirose et al. | 424/58 |
| 5,240,732 A | 8/1993 | Ueda | 426/597 |
| 5,384,123 A | 1/1995 | Metsada | 424/732 |
| 5,411,733 A | 5/1995 | Hozumi et al. | 424/727 |
| 5,466,443 A | 11/1995 | Ho et al. | 424/70.6 |
| 5,466,452 A | 11/1995 | Whittle | 424/750 |
| 5,494,668 A | 2/1996 | Patwardhan | 424/756 |
| 5,547,671 A | 8/1996 | Duthinh | 424/728 |
| 5,585,101 A | 12/1996 | Portman | 424/728 |
| 5,595,743 A | 1/1997 | Wu | 424/728 |
| 5,707,630 A | 1/1998 | Morrow | 424/733 |
| 5,744,187 A | 4/1998 | Gaynor | 426/599 |
| 5,804,168 A | 9/1998 | Murad | 424/59 |
| 5,854,291 A | 12/1998 | Laughlin et al. | 514/626 |
| 5,856,361 A | 1/1999 | Holt et al. | 514/627 |
| 5,882,672 A | 3/1999 | Kojima et al. | 424/438 |
| 5,888,514 A | 3/1999 | Weisman | 424/94.1 |
| 5,895,652 A | 4/1999 | Giampapa | 424/195.17 |
| 5,904,924 A | 5/1999 | Gaynor et al. | 424/195.17 |
| 5,908,628 A | 6/1999 | Hou | 424/735 |
| 5,908,857 A | 6/1999 | Suzuki | 514/410 |
| 5,916,542 A | 6/1999 | Fossati | 424/59 |
| 5,916,565 A | 6/1999 | Rose et al. | 424/756 |
| 5,955,102 A | 9/1999 | Gorenbein et al. | 424/451 |
| 5,976,548 A | 11/1999 | Hsia et al. | 424/735 |
| 6,027,728 A | 2/2000 | Yuen | 424/728 |
| 6,030,980 A | 2/2000 | Suzuki | 514/281 |

FOREIGN PATENT DOCUMENTS

| | | |
|---|---|---|
| CN | 1207927 | 2/1999 |
| CN | 1207930 | 2/1999 |
| CN | 1216254 | 5/1999 |

OTHER PUBLICATIONS

Botte et al., (1996) "Recurrent Carpal Tunnel Syndrome." *Hand Clin.* 12(4):731–743.
Bergqvist and Knave, (1994) "Eye discomfort and work with visual display terminals." *Scand. J. Work Environ. Health*, 20(1):27–33.
Borenstein, (1992) "Epidemiology, etiology, diagnostic evaluation, and treatment of low back pain." *Cur. Opin. Rheumatol* 4(2):226–232.
De Smet et al., (1995) "Value of Clinical Provacative Tests in Carpal Tunnel Syndrome." *Acta. Orthop. Belg.* 61(3):177–182.
Deyo and Phillips, (1996) "Low Back Pain" *Spine* 21:2826–2832.
Hikichi, T. et al., (1995) "Prevalence of dry eye in Japanese eye centers" *Graefes Arch. Clin. Exp. Ophthalmol.*, 223 (9):555–558.
Kirsner, R. S. and Federman, D.G., (1998) "Video Display Terminals: Risk of Electromagnetic Radiation" *South Med. J*, 91 (1):12–16.
Kuschner et al., (1992) "Tinel's Sign and Phalen's Test in Carpal Tunnel Syndrome." *Orthopedics*, 15(11):1297–1302.
Melhorn (1994) "CTD: Carpal Tunnel Syndrome, The Facts and Myths." *Kans. Med.* 95(9):189–192.
Remington's Pharmaceutical Sciences, 18th Edition, Mack Publishing (1990), pp. xv–xvi (Table of Contents.).
Salibello and Nilsen, (1995) "Is there a typical VDT patient? A demographic analysis." *J. Am. Optom Assoc.*, 66(8):479–483.
Sheedy, J.E., (1992) "Vision problems at video display terminals: a survey of optometrist" *J. Am. Optom. Assoc.*, 63 (10):687–692.
Sternback, (1999) "The Carpal Tunnel Syndrome." *J. Emerg. Med.* 17(3):519–523.
Szabo, (1998) "Carpal Tunnel Syndrome as a Repetitive Motion Disorder." *Clin. Orthop.* 351:78–89.

*Primary Examiner*—Jean C. Witz
(74) *Attorney, Agent, or Firm*—Morrison & Foerster LLP

(57) ABSTRACT

Compositions and methods for enhancing the effects of therapeutic compositions are provided. The compositions comprise singly or in combination herbals, natural nutritional supplements, minerals and vitamins.

1 Claim, No Drawings

COMPOSITIONS AND METHODS FOR ENHANCING THERAPEUTIC EFFECTS

CROSS-REFERENCE TO RELATED APPLICATIONS

This application claims the benefit of U.S. Provisional Application Serial No. 60/208,990, filed Jun. 1, 2000, hereby incorporated in its entirety by reference.

TECHNICAL FIELD

This invention relates to compositions and methods for enhancing therapeutic effects. More specifically, it relates to nutraceutical compositions for enhancing the therapeutic effects of another composition, and methods for enhancing therapeutic effects.

BACKGROUND ART

The need for enhancement of therapeutic effects of therapeutic substances or compositions is particularly apparent where conventional herbal and natural nutritional supplements are used to achieve these effects. These substances act slowly, and are considered primarily to provide individuals with long term benefits rather than short term or immediate improvement in the medical condition in question. Although pharmaceutical drugs have generally been considered to be more effective in treating acute conditions, this treatment often has significant side effects. Non-pharmaceutical alternatives, such as nutraceuticals, are often preferred because of their safer or more long-lasting effects. This usually means, however, that in choosing these alternative approaches, the treated individual has to forego more immediate alleviation of symptoms that might otherwise have been achievable through the use of pharmaceuticals.

It would, therefore, clearly be advantageous to have herbal and natural nutritional supplements that can provide therapeutic effects similar in intensity and immediacy to pharmaceutical drugs, while continuing to provide long term health benefits and with the avoidance of significant side effects. The invention described and claimed in this specification provides this advantage by presenting compositions and methods for enhancing the therapeutic effects of conventional herbal and natural nutritional supplements.

All references cited herein, including patent applications and publications, are incorporated by reference in their entirety.

DISCLOSURE OF THE INVENTION

Compositions and methods for enhancing effects of therapeutic compositions are provided. The compositions comprise substances in quantities that are effective for enhancing the therapeutic effects of compositions with which they are administered in combination. Methods of enhancing therapeutic effects of a composition comprising administration of the claimed compositions are also provided. Methods of making compositions of the invention are also provided.

Accordingly, in one aspect, the invention provides a first composition for enhancing the therapeutic effects of a second composition, said first composition comprising a substance selected from the group consisting of a member of the botanical group Daemonorops and a member of the botanical group Corydalis.

In another aspect, the invention provides a first composition for enhancing the therapeutic effects of a second composition, said first composition comprising a member of the botanical group Daemonorops and a member of the botanical group Corydalis.

In one embodiment, the invention provides a composition selected from a group consisting of the first compositions of the aspects of the invention described in the preceding paragraphs, further comprising a substance selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C. Thus, for example, in one embodiment, a composition comprises a member of the botanical group Daemonorops and a member of the botanical group Panax. In some of these embodiments, the composition comprises *xuejie* and *shanqi*. In another example, a composition comprises a member of the botanical group Corydalis and a member of the botanical group Panax. In some of these embodiments, the member of the botanical group Corydalis is *yanhusuo* and the member of the botanical group Panax is *shanqi*.

In another embodiment, the invention provides a composition selected from a group consisting of the aspects of the invention described in the preceding paragraphs, further comprising 2 substances selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C.

In another embodiment, the invention provides a composition selected from a group consisting of the aspects of the invention described in the preceding paragraphs, further comprising 3 substances selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C.

In another embodiment, the invention provides a composition selected from a group consisting of the aspects of the invention described in the preceding paragraphs, further comprising 4 substances selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C.

In another embodiment, the invention provides a composition selected from a group consisting of the aspects of the invention described in the preceding paragraphs, further comprising 5 substances selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C.

In another embodiment, the invention provides a composition selected from a group consisting of the aspects of the invention described in the preceding paragraphs, further comprising 6 substances selected from the group consisting of a member of the botanical group Paeonia, a member of the botanical group Panax, a member of the botanical group glycyrrhiza, white willow bark, a member of the botanical group Cimici fuga, L-carnitine, vitamin E and vitamin C.

In another embodiment, the invention provides a composition selected from a group consisting of the aspects of the invention described in the preceding paragraphs, further comprising 7 substances selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C.

In another embodiment, the invention provides a composition selected from a group consisting of the aspects of the invention described in the preceding paragraphs, further comprising a member of the botanical group Paeonia, a member of the botanical group Panax, a member of the botanical group glycyrrhiza, white willow bark, a member of the botanical group Cimicifuga, L-carnitine, vitamin E and vitamin C.

In some embodiments of the compositions of the aspects of the invention. described in the preceding paragraphs, the member of the botanical group Daemonorops is *xuejie* and/or the member of the botanical group Corydalis is *yanhusuo*. In some embodiments of the compositions of the aspects and embodiments of the invention described in the preceding paragraphs, the member of the botanical group Daemonorops is *xuejie*, the member of the botanical group Corydalis is *yanhusuo*, the member of the botanical group Paeonia is *baishaoyao*, the member of the botanical group Panax is *shanqi*, the member of the botanical group glycyrrhiza is *gancao*, and/or the member of the botanical group Cimicifuga is black cohosh.

Accordingly, in one aspect, the invention provides a first composition for enhancing the therapeutic effects of a second composition, said first composition comprising a substance selected from the group consisting of *xuejie* and *yanhusuo*.

In another aspect, the invention provides a first composition for enhancing the therapeutic effects of a second composition, said first composition comprising *xuejie* and *yanhusuo*.

In one embodiment, the invention provides a composition selected from the group consisting of the first compositions of the aspects of the invention described in the preceding paragraphs, further comprising a substance selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising 2 substances selected from the group consisting of *baishaoyao, shanqi, gancao*, white willow bark, black cohosh root, L-carnitine, vitamin E and vitamin C.

In another embodiment, the invention provides a composition selected from a group consisting of the first compositions of aspects of the invention described in the preceding paragraphs, further comprising 3 substances selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising 4 substances selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising 5 substances selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising 6 substances selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising 7 substances selected from the group consisting of *baishaoyao, shanqi, gancao*, white willow bark, black cohosh root, L-carnitine, vitamin E and vitamin C.

In another embodiment, the invention provides a composition selected from the group consisting of the first compositions of the aspects of the invention described in the preceding paragraphs, further comprising *baishaoyao, shanqi, gancao*, white willow bark, black cohosh root, L-carnitine, vitamin E and vitamin C.

In one embodiment, the invention provides a first composition for enhancing therapeutic effects of a second composition comprising *xuejie, yanhusuo, baishaoyao, shanqi, gancao*, white willow bark, black cohosh root, L-carnitine, vitamin E and vitamin C.

In some embodiments of the compositions of the invention described herein, said compositions further comprise zinc and/or selenium.

In various aspects and embodiments of the compositions of the invention, the second composition whose therapeutic effects are enhanced by the compositions of the invention is effective for treating a condition selected from the group consisting of an eye discomfort condition, a wrist discomfort condition, a neck and shoulder discomfort condition, and a back and leg discomfort condition. In some embodiments, compositions of the invention are effective for enhancing cellular metabolism. In some embodiments, the compositions of the invention are effective for enhancing blood circulation, reducing cellular/tissue inflammation and/or reducing pain.

In one aspect, the invention provides methods for enhancing effects of a therapeutic composition comprising co-administering an effective amount of a composition selected from the group consisting of the compositions of the invention disclosed in the preceding paragraphs with said therapeutic composition, whereby the effects of said therapeutic composition are enhanced.

In still another aspect, the invention provides methods of making a composition for enhancing effects of a therapeutic composition, said method comprising combining at least one (for example, 1 or 2) substance (preferably in an effective amount) selected from the group consisting of a member of the botanical group Daemonorops and a member of the botanical group Corydalis with at least one (preferably 1, 2, 3, 4, 5, 6, 7 or 8) substance (preferably in an effective amount) selected from the group consisting of a member of the botanical group Paeonia, a member of the botanical group Panax, a member of the botanical group glycyrrhiza, white willow bark, a member of the botanical group Cimicifuga, L-carnitine, vitamin E and vitamin C. In some embodiments, the methods comprise combining a member of the botanical group Daemonorops and a member of the botanical group Corydalis. In various embodiments of the these methods, the member of the botanical group Daemonorops is *xuejie*, the member of the botanical group Corydalis is *yanhusuo*, the member of the botanical group Paeonia is *baishaoyao*, the member of the botanical group Panax is *shanqi*, the member of the botanical group glycyrrhiza is

*gancao*, and/or the member of the botanical group Cimicifuga is black cohosh. In some embodiments, said combining is by mixing (such as by stirring, agitation or vibration). In some embodiments, the substances are packaged in the form of capsules, preferably in size "0", "00", "000", "1", "2", "3" or "4." In yet other embodiments, the substances are combined in powder form, preferably to at least 30%, 60%, or 90% mixture consistency, or to homogeneity.

MODES FOR CARRYING OUT THE INVENTION

The present invention discloses compositions comprising single or multiple substances that are effective and safe for enhancing the therapeutic effects of another composition when administered in combination. The invention further provides methods for enhancing therapeutic effects of compositions comprising co-administering the compositions of this invention with a therapeutic composition.

Definitions

The term "treating," "treatment," and variations thereof, as used in this specification, refers to an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

A "treatment effect" or "therapeutic effect" is manifested if there is a change in the condition being treated, as measured by the criteria constituting the definition of the terms "treating" and "treatment." There is a "change" in the condition being treated if there is at least 10% improvement, preferably at least 25%, more preferably at least 50%, even more preferably at least 75%, and most preferably at least 100%. The change can be based on improvements in the severity of the treated condition in an individual, or on a difference in the frequency of improved conditions in populations of individuals with and without treatment with the therapeutic compositions with which the compositions of the present invention are administered in combination. A "therapeutic composition" is a composition administered to achieve a treatment or therapeutic effect.

The term "enhancing," and variations thereof, as used in this specification, refers to an increase in the therapeutic effects of a composition above those normally obtained when the therapeutic composition is administered without the compositions of this invention. "An increase in the therapeutic effects" is manifested when there is an acceleration and/or increase in intensity and/or extent of the therapeutic effects obtained with a therapeutic composition. It also includes extension of the longevity of therapeutic benefits. It can also manifest where a lower amount of the therapeutic composition is required to obtain the same benefits and/or effects when it is co-administered with compositions provided by the present invention as when a higher amount of the therapeutic composition is administered alone. The enhancing effect preferably, but not necessarily, results in treatment of acute symptoms for which the therapeutic composition alone is not effective or is less effective therapeutically. Enhancement is achieved when there is at least a 10% increase in the therapeutic effects when a composition of the present invention is co-administered with a therapeutic composition compared with administration of the therapeutic composition alone. Preferably the increase is at least 25%, more preferably at least 50%, even more preferably at least 75%, most preferably at least 100%.

An "effective amount" is an amount of a composition or substance(s) sufficient to enhance the effects of a therapeutic composition after one or more administrations of that amount. An effective amount can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

"Co-administering" or "co-administration" of compositions, as used herein, refers to the administration of a composition of the present invention and a therapeutic composition within a certain time period. The time period is preferably 12 hours, more preferably 6 hours, still more preferably 3 hours. These terms most preferably mean the compositions are administered together.

"Blood circulation," as used herein, generally refers to the course of the blood from the heart through the arteries, capillaries, and veins back again to the heart. "Microcirculation," as used herein, refers to the circulation of blood in and/or through microvessels (such as capillaries) and/or circulation of blood within a tissue/organ. Blood circulation or microcirculation is "enhanced" when at least one of the criteria that define blood circulation and/or microcirculation is enhanced. These criteria are known in the art, for example, plasma viscosity, blood pressure and blood viscosity. There is enhancement of any of these criteria when there is preferably at least 10%, more preferably at least 30%, even more preferably at least 50%, and most preferably at least 75% increase in the measurement of any of these criteria.

"Metabolism," "cellular metabolism," and "intracellular metabolism," as used herein, refers to metabolic reactions and/or processes in the body, as understood in the art. It generally refers to the sum of the chemical and/or physical changes occurring in tissue, consisting of anabolism (those reactions that convert small molecules into large) and catabolism (those reactions that convert large molecules into small), including both endogenous large molecules as well as biodegradation of xenobiotics. Metabolism, cellular metabolism, and intracellular metabolism is "enhanced" when at least one of the criteria that define metabolism is enhanced. These criteria are known in the art, for example, production rate/level of pyruvate, acetyl CoA, and adenosine triphosphate. There is enhancement of any of these criteria when there is preferably at least 10%, more preferably at least 30%, even more preferably at least 50%, and most preferably at least 75% increase in the measurement of any of these criteria.

"Individual," as used herein, refers to a vertebrate, preferably a mammal, more preferably a human.

A "botanical group," as used herein, refers to a group of botanical entities that are capable of providing similar physiological effect(s) in the compositions of the invention.

These botanical entities may or may not belong to the same botanical classification (such as genus, family).

"Xuejie," as used herein, refers to extracts of *xuejie*. It is also known as *sanguis draconis* and *Daemonorops droco* B1. A member of the botanical group Daemonorops is a substance that is capable of providing a similar physiological effect(s) as that provided by *xuejie* in the compositions of the invention, and is preferably selected from a group comprising *Sanguis draconis Daemonorops droco* B1.; *Daemonorops draco* B1 (*xuejie* ); *Dracaena cambodiana* Pierre; *Dracaena cinnabari* Balf; *Dracaena draco* Linn.; *Dracaena schizantha* Baker; *Dracaena dihynophyllus; Dracaena micracanthus* Becc.; *Dracaena propinqus* Becc.; *Dracaena draconcellus* Becc.; *Dracaena motleyi* Becc.; *Dracaena sparsiflorus* Becc.; *Pterocarpus draco* Linn.; *Croton draco* Schlecht; *Croton hibiscifolius* kunth; *Croton sanguifluus* H. B. et K Nov.; *Croton gossypiifolius* Vahl.

"Yanhusuo," as used herein, refers to extracts of *yanhusuo*. It is also known as *Rhizoma corydalis yanhusuo* and *Corydalis yanhusuo* W. T. Wang. A member of the botanical group Corydalis is a substance that is capable of providing a similar physiological effect(s) as that provided by *yanhusuo* in the compositions of the invention, and is preferably selected from a group comprising *Rhizoma corydalis yanhusuo; Corydalis yanhusuo* W. T. Wang.; *Corydalis yanhusuo* W. T. Wang (*yanhusuo*); *Corydalis amabilis* Migo; *Corydalis amabigua* Cham. et Schlecht. Var *amurensts* Maxim; *Corydalis turtschaninovii* Bess.; *Corydalis turtschaninovii* f. *yanhusuo; Corydalis schangini* (Pall.) B.; *Corydalis glaucescens* Rgl.; *Corydalis ledebouriana* Kar. Et Kir.

"Baishaoyao," as used herein, refers to extracts of *baishaoyao*. It is also known as *Radix paeoniae lactiflorae* and *paeonia lactiflora* Pall. A member of the botanical group Paeonia is a substance that is capable of providing a similar physiological effect(s) as that provided by *baishaoyao* in the compositions of the invention, and is preferably selected from a group comprising *Radix paeoniae lactiflorae; Radix paeoniae rubra; Radix paeoniae veitchii; Paeonia lactiflora* Pall; *Paeonia albriflora* Pall; *Paeonia veitchii* Lynch; *Paeonia lactiflora* Pall. Var. *trichocarpa* (Bunge) Stem.; *Paeonia obovata.* Maxim; *Paeonia anomala; Paeonia hybrida* Pall; *Paeonia veitchii* var *woodwardii; Paeonia edulis* (Salisb.); *Paeonia officinalis* Thunb.

"Shanqi," as used herein, refers to extracts of *shanqi*. It is also known as *Radix Notoginsheng* and *Panax notoginsheng* (Burk.) F. H. Chen. A member of the botanical group Panax is a substance that is capable of providing a similar physiological effect(s) as that provided by *shanqi* in the compositions of the invention, and is preferably selected from a group comprising *Radix notoginsheng; Panax notoginsheng* (Burk.) F. H. Chen.; *Panax notoginseng* (Burk.) F. H. Chen (*Shanqi*); *Panax pseudo-ginseng* Wall.var.*notoginseng* (Burk) Hoo et Tseng; *Panax ginseng* C. A. Mey (*P.schinseng* Nees); *Panax guinquefolium* L.; *Radix ginseng; Panax ginseng* C. A. Mey; *Panax schin-seng* Nees; *Panax schinseng.; Panax schinseng; Panax pseudoginseng; Panax pseudoginseng japonicus* (C. A. Mey.) Hoo.&Tseng.; *Panax repens.* Max.; *Panax pseudoginseng japonicus; Panax pseudoginseng* ssp. *Japonicus; Panax pseudoginseng* subsp.; *Panax japonicus; Panax pseudoginseng* var. *japonicus; Panax pseudo-ginseng; Panax ginseng; Panax schinseng Acanthopanax sentocosus* (Rupr. et Maxim.); *Eleutherococus senticosus* (Rupr. et Maxim.).; *Eleutherococus senticosus; Acanthopanax senticosus; Acanthopanax seticosus* Harms; *Acantherococus senticocus* (Rupr.et.Maxim) Harms.; *Eleutherococus senticocus* (Rupr. Et Maxim) Maxim.; *Echinopanax elatus* Nakai; *Hedera senticosa*.

"Gancao," as used herein, refers to extracts of *gancao*. It is also known as *Radix glycyrrhizae uralensis, Glycyrrhiza uralensis* Fischer or licorice root. A member of the botanical group glycyrrhiza is a substance that is capable of providing a similar physiological effect(s) as that provided by *gancao* in the compositions of the invention, and is preferably selected from a group comprising *Radix glycyrrhizae uralensis; Glycyrrhiza uralensis* Fischer; *Glycyrrhiza uralensis* Fisch (*Gan cao*); *Glycyrrhiza glabra* L.; *Glycyrrhizainflata Batal.; Glycyrrihiza korshiskyi* G. Hrig.; *Glycyrrhiza aspera* Pall; *Glycyrrhiza yunnanensis* Cheng f. et L. K. Tai.; *Glycyrrhiza malensis*.

"White willow bark," as used herein, refers to extracts of white willow bark. It is also known as *Saliz alba caertilea*.

"Black cohosh root," as used herein, refers to extracts of black cohosh root. It is also known as rhizome of *Cimicifuga racemosa* or *Cimicifuga racemosa*. A member of the botanical group Cimicifuga is a substance that is capable of providing a similar physiological effect(s) as that provided by black cohosh root in the compositions of the invention, and is preferably selected from a group comprising *Cimicifuga racemosa; Cimicifuga cordifolia; Cimicifuga racemosa* var. *cordifolia; Cimicifuga heracleifolia* Komar.; *Cimicifuga dahurica* (Turcz) Maxim; *Cimicifuga foetida* L.; *Actaea racemosa*.

"L-carnitine," as used herein, refers to the biochemical molecule known as such by persons of skill in the art. It is generally known as a zwitterionic compound formed from lysine. It also refers to related molecules such as L-acetyl-carnitine.

"Vitamin C," as used herein, refers to ascorbic acid and salts thereof.

"Vitamin E," as used herein, refers to D alpha-tocopherol, preferably in succinate form.

"Zinc," as used herein, refers to the form(s) of the mineral known to persons of skill in the art to be therapeutically effective in the body of the individual. It is preferably provided as zinc gluconate.

"Selenium," as used herein, refers to the form(s) of the mineral known to persons of skill in the art to be therapeutically effective in the body of the individual. It is preferably provided as selenium aminoate.

"Extract," as used herein, refers to the substances obtained from the specified source plant, or parts thereof (for e.g., root, bark, leaves). Any method of extraction that yields extracts that retain the biological activity of the substances contained in the extract source can be used to produce extracts used in this invention. Preferably, the ingredients of the compositions of the present invention are extracted as an aqueous solution. The extraction is preferably performed under conditions of high pressure, preferably from 0.5 to 12 bar, more preferably 1 to 10 bar, most preferably 3 to 7 bar, and preferably at elevated temperatures (preferably within a range of 15° C. to 120° C., more preferably 30° C. to 100° C., most preferably 45° C. to 75° C.). The extract is preferably treated to yield a form suitable for mixing of two or more substances. The form is preferably a dried powder. The powder form is yielded from preferably at least about a 1:10, more preferably at least about a 1:8, most preferably at least about a 1:5 concentrate of the starting solution. Concentration to powder form is preferably achieved by evaporation to yield a dried powder form. The extracts used in this invention can also be obtained from commercial sources such as Sun Ten Laboratories (Irvine, Calif.), Qualiherb (Cerritos, Calif.), Mayway (Oakland, Calif.), Ming Tong Herb (Oakland, Calif.) and Acta (Sunnyvale, Calif.). It is understood that any method or conditions known in the art to yield extracts comparable in effectiveness in enhancing therapeutic effects to those produced by the preceding preferred extraction method can be used for the purposes of this invention.

Formulation of the Composition

Each substance contained in the compositions provided by this invention is provided in an amount that lies within specific quantitative ranges herein disclosed to be effective for enhancing the therapeutic effects of a therapeutic composition.

According to the present invention, an effective amount of a composition comprises preferably from 100 to 1500 mg, more preferably 300 mg to. 1200 mg, most preferably 600 mg to 900 mg of a member of the botanical group Daemonorops (such as *xuejie* ); and/or preferably 50 mg to 1000 mg, more preferably 200 mg to 800 mg, most preferably 400 mg to 600 mg of a member of the botanical group Corydalis (such as *yanhusuo*).

In the various embodiments of the invention, the compositions further comprise preferably from 50 mg to 1000 mg, more preferably 200 mg to 800 mg, most preferably 400 mg to 600 mg of a member of the botanical group Paeonia (such as *baishaoyao*); preferably 200 mg to 3000 mg, more preferably 500 mg to 2000 mg, most preferably 800 mg to 1500 mg of a member of the botanical group Panax (such. as *shanqi*); preferably 50 mg to 1000 mg, more preferably 200 mg to 800 mg, most preferably 400 mg to 600 mg of a member of the botanical group glycyrrhiza (such as *gancao*); preferably 5 mg to 150 mg, more preferably 10 mg to 120 mg, most preferably 75 mg to 100 mg white willow bark; preferably 5 mg to 150 mg, more preferably 40 mg to 120 mg, most preferably 75 mg to 100 mg of a member of the botanical group Cimicifuga (such as black cohosh root); preferably 30 mg to 600 mg, more preferably 120 mg to 500 mg, most preferably 250 mg to 400 mg,L-carnitine; preferably 10 mg to 250 mg, more preferably 80 mg to 300 mg, most preferably 120 mg to 200 mg vitamin E; and/or preferably 20 mg to 400 mg, more preferably 80 mg to 300 mg, most preferably 120 mg to 200 mg vitamin C.

Thus, for example, a composition may comprise preferably from 100 to 1500 mg, more preferably 300 mg to 1200 mg, most preferably 600 mg to 900 mg of a member of the botanical group Daemonorops (such as *xuejie*), and preferably 200 mg to 3000 mg, more preferably 500 mg to 2000 mg, most preferably 800 mg to 1500 mg: of a member of the botanical group Panax (such as *shanqi*). In another example, a composition comprises preferably 50 mg to 1000 mg, more preferably 200 mg to 800 mg, most preferably 400 mg to 600 mg of a member of the botanical group Corydalis (such as *yanhusuo*), and preferably 200 mg to 3000 mg, more preferably 500 mg to 2000 mg, most preferably 800 mg to 1500 mg of a member of the botanical group Panax (such as *shanqi*).

Selection of suitable members of a particular botanical group to be included in a composition can be achieved using methods known in the art. For example, a suitable member of the botanical group Panax would be expected to be capable of providing a similar physiological effect(s) as that provided by *shanqi* in a composition of the invention. Such a member can be selected based on, for example, whether it is known, shown and/or suspected to possess said similar physiological effect(s). Thus, for example, a determination of whether a candidate substance can be a member of the botanical group Panax can be done based on, for example, a similar pharmacological or medicinal classification for both the candidate substance and *shanqi*. However, the activity and/or function provided by a particular substance, such as *shanqi*, need not be identified or specified. A determination of whether a candidate substance can be a member of a particular botanical group, for example the Panax group, can also be empirical, for example, by substituting said candidate substance for *shanqi* in a composition, and assessing the relevant therapeutic effect(s)

of the composition. Such a determination can be done using methods and techniques known in the art.

According to this invention, the compositions can be formulated in whatever form that retains the efficacy of the compositions for enhancing the therapeutic effects of another composition. Preferably, the compositions are packaged in the form of capsules. The capsules are preferably of size "0", "00", "000", "1", "2", "3" or "4." A preferred method for packaging into capsules involves mixing substances (extracts, vitamin and minerals) that are preferably in powder form. The substances are preferably mixed to at least 30%, more preferably to at least 60%, even more preferably to at least 90% mixture consistency, and most preferably to homogeneity. The substances in powder form are provided in the initial mixture at ratios according to the effective quantities disclosed above. Methods for mixing the substances are known in the art, including, but not limited to, stirring, agitation or vibration achieved manually or through the aid of a machine. A preferred mixing machine is a V-mixer, preferably of 100 to 1400-liter size, more preferably of 150 to 1300-liter size, and most preferably of 200 to 1200-liter size. Preferably, the resulting powder mixture is filtered to screen out particulates (i.e., anything that a person of skill in the art would recognize to be larger than powder size). A preferred filter is a ¹/₂₀-inch particle size filter. Preferably, the filtered mixture is packaged into capsules according to the weight desired for each capsule. Preferably, the capsule is of size "00". The weight of mixture per capsule is preferably from 5 mg to 1000 mg, more preferably 100 mg to 800 mg, even more preferably 400 mg to 700 mg. It is understood that other physical forms of the compositions of this invention suitable for administration to an individual can also be used, including, for example, tablets, salves or liquids, as long as the compositions can be delivered to the target tissues in the body where the compositions in the preferred form described above exert their effects.

The ingredients of the compositions can be mixed with pharmaceutically acceptable solvents, excipients and/or filler substances. These materials are known in the art, and are described in sources such as *Remington's Pharmaceutical Sciences,* 18th Edition, Mack Publishing (1990).

Combining Compositions of the Present Invention with a Therapeutic Composition

Compositions in any of the physical forms described above can be administered by any method known to one of skill in the art, but oral administration is preferred. The compositions are preferably administered in capsule form.

An effective amount of a composition is provided preferably in from 1 to 8 administrations, more preferably in from 2 to 6 administrations, and most preferably in from 3 to 5 administrations. Administration of an effective amount is preferably completed within 24 hours. A composition can be ingested alone, or with any other substance, such as a liquid, that aids ingestion of the compositions. Ingestion of the compositions can be before or after food consumption. The compositions of the present invention can be combined with any therapeutic composition to enhance the effects of the therapeutic composition in treating diseases or discomfort conditions.

In preferred embodiments, the present compositions are combined with compositions that are effective in treating eye discomfort syndromes, pains and/or discomfort in joints such as the wrist, pains and/or discomfort in the neck and/or shoulder, or pains and/or discomfort in the back and leg. We have discovered that the compositions of the present invention are particularly effective in enhancing the therapeutic effects of the compositions disclosed in co-pending patent applications entitled "Compositions And Methods For Treating Eye Discomfort" (U.S. provisional Application Ser. No. 60/208,783; U.S. patent application Ser. No. 09/872,375, filed even date herewith); "Compositions And Methods For Treating Hand And Wrist Discomfort" (U.S. provisional Application Ser. No. 60/208,991; U.S. patent application Ser. No. 09/873,175, filed even date herewith); "Compositions and Methods For Treating Neck And Shoulder Discomfort" (U.S. provisional Application Ser. No. 60/208,797; U.S. patent application Ser. No. 09/872,368, filed even date herewith); and "Compositions and Methods For Treating Back And Leg Discomfort" (U.S. provisional Application Ser. No. 60/208,793; U.S. patent application Ser. No. 09/872,609, filed even date herewith), all of which are hereby in their entirety incorporated by reference. The present compositions enhance the therapeutic effects of these compositions for treating conditions such as eye discomfort syndromes, wrist strain or pain, neck or shoulder pain, and back or leg pain. Without wishing to be bound by theory, the compositions of the present invention enhance therapeutic effects by relaxing muscles and tendons, activating the flow of Qi and blood in the meridian and collaterals according to Chinese medicine, relieving rigidity of muscles and activating collaterals and promoting blood circulation, enriching blood and nourishing muscles and tendons, and arresting bleeding by removal of stasis, thereby promoting the delivery of the therapeutic compositions to target tissues when the therapeutic compositions are co-administered with the present compositions.

Other medical conditions for which the compositions of the present invention are particularly useful include post-trauma muscle spasms, bleeding (internal and external), sciatic pain, swelling and bleeding due to injury and bruising, inflammatory conditions, general and specific pain conditions. The present compositions enhance the efficacy of compositions used to treat these conditions.

The preferred timing of co-administration is administration of the compositions of this invention at the same time as the administration of the therapeutic compositions. However, the timing of co-administration can be varied according to the needs of the individual, or in accordance with the empirical determination or experience of the health care professional or individual.

EXAMPLES

Example 1

An Illustrative Example of the Formulation of a Single "00" Capsule, and the Production Thereof A composition shown to enhance the effects of a therapeutic composition for treating neck and shoulder pains contained substances in the indicated quantities as listed in Table 1.

TABLE 1

| SUBSTANCE [Commercial Source] | AMOUNT (mg) |
|---|---|
| Xuejie [Min Tong Herb, Oakland, CA] | 133 |
| Yanhusuo [Mayway, Oakland, CA] | 83 |
| Baishaoyao [Qualiherb, Cerritos, CA] | 83 |
| Shanqi [Sun Ten, Irvine, CA] | 250 |
| Gancao [Qualiherb, Cerritos, CA] | 83 |
| White willow bark [Acta, Sunnyvale, CA] | 10 |
| Black cohosh root [Acta, Sunnyvale, CA] | 10 |
| L-carnitine [Acta, Sunnyvale, CA] | 50 |
| Vitamin E (D Alpha-Tocopherol succinate) [Acta, Sunnyvale, CA] | 21.19 |
| Vitamin C [Acta, Sunnyvale, CA] | 30 |

Capsules containing the composition above were manufactured according to the method used by the commercial manufacturer, Acta (Sunnyvale, Calif.). Briefly, the substances listed above, in powder form and obtained from the commercial sources indicated, were mixed in input amounts in accordance to the ratio of the substances in the composition as a whole. Mixing was accomplished with a V-mixer, grinding for 15 to 30 minutes, at a speed of 15 to 30 rpm (rounds per minute), to produce a homogenous mixture of the input substances. Particulates (non-powder forms) were then filtered out with a $\frac{1}{20}$-inch particle size filter that separated particulates from the powder. 671 mg of the filtered mixture was then packaged into each size "00" capsule.

Example 2

Illustrative Example of Enhancement of Therapeutic Effects of a Composition for Treating Neck or Shoulder Discomfort 11 individuals with neck or shoulder pain symptoms were treated with the composition exemplified in Example 1 in combination with the composition set forth in Table 2. The composition of Table 2 is exemplified as Example 1 of co-pending patent application entitled "Compositions and Methods For Treating Neck And Shoulder Discomfort" (which is hereby incorporated herein by reference in its entirety). The individuals were instructed to fill out a clinical questionnaire to assess efficacy of treatment with these compositions over time. They were instructed to assess frequency of pain (e.g., occasional, intermittent, or constant) as a primary criterion for pain severity. They were administered the compositions for between 3 days and 3 weeks, at a daily dosage of from 2 to 9 capsules of the composition of Table 2, and at a daily dosage of from 1 to 9 capsules of the composition of Example 1.

TABLE 2

A Composition For Treating Neck And Shoulder Discomfort

| SUBSTANCE [commercial source] | AMOUNT (mg) |
|---|---|
| Huangqi [Mayway, Oakland, CA] | 33 |
| Dangquiwei [Mayway, Oakland, CA] | 33 |
| Weilingxian [ Qualiherb, Cerritos, CA] | 67 |
| Gegen [Qualiherb, Cerritos, CA] | 167 |
| Guizi [Qualiherb, Cerritos, CA] | 167 |
| Baishaoyao [Qualiherb, Cerritos, CA] | 167 |
| Gancao [Qualiherb, Cerritos, CA] | 17 |
| Dazao [Mayway, Oakland, CA] | 17 |
| Bilberry [Acta, Sunnyvale, CA] | 10 |

TABLE 2-continued

A Composition For Treating Neck And Shoulder Discomfort

| SUBSTANCE [commercial source] | AMOUNT (mg) |
|---|---|
| Ginger [Qualiherb, Cerritos, CA] | 17 |
| Vitamin B-1 (thiamine) [Acta, Sunnyvale, CA] | 5 |
| Vitamin B-2 (riboflavin) [Acta, Sunnyvale, CA] | 5 |
| Vitamin B-6 (pyridoxine) [Acta, Sunnyvale, CA] | 15 |
| Vitamin B-12 (cobalamin) [Acta, Sunnyvale, CA] | 0.0125 |
| Vitamin C (ascorbic acid) [Acta, Sunnyvale, CA] | 30 |
| Vitamin E (D alpha-tocopherol succinate) [Acta, Sunnyvale, CA] | 21.19 |
| White willow bark [Acta, Sunnyvale, CA] | 10 |
| Quercitin [Acta, Sunnyvale, CA] | 25 |
| Selenium aminoate [Acta, Sunnyvale, CA] | 20 |

Severity of neck pain was graded on a scale of 0 to 10. 0 was defined as normal neck condition and 10 was defined as severe pain. The results showed a clear and significant decrease in severity, and in some cases complete clearance, of pain by the end of the study. By comparing these results to the results expected from a study wherein individuals are administered the composition of Table 2 alone, it would be clear that the composition of Example 1 enhances the therapeutic effects of the composition of Table 2 in treating neck pain.

Severity of shoulder pain was graded on a scale of 0 to 10. 0 was defined as normal shoulder condition and 10 was defined as severe pain. The results showed a clear and significant decrease in severity, and in some cases complete clearance, of pain by the end of the study. By comparing these results to the results expected from a study wherein individuals are administered the composition of Table 2 alone, it would be clear that the composition of Example 1 enhances the therapeutic effects of the composition of Table 2 in treating shoulder pain.

It is understood that the enhancing effect of the compositions of the present invention can be demonstrated for any therapeutic composition using any study protocol similar to the one described in this Example.

Example 3

Illustrative Example of Enhancement of Therapeutic Effects of a Composition for Treating Hand or Wrist Discomfort An individual who suffered two separate bouts of wrist pain was treated during the course of one bout with the composition set forth in Table 3 (Bout A), and during the course of the other bout with the composition of Table 3 in combination with the composition exemplified in Example 1 of the instant specification (Bout B). The composition of Table 3 is exemplified as Example 1 of co-pending patent application entitled "Compositions And Methods For Treating Hand And Wrist Discomfort" (which is hereby incorporated herein by reference in its entirety). In Bout A, 5 dosages of 2 capsules per dosage, followed by 7 dosages of 1 capsule per dosage, of the composition of Table 3 were administered. In Bout B, the same dosage amounts were administered for the same duration, except that the composition of Example 1 of the instant specification was co-administered (simultaneously) at 2 capsules per dosage for the first 5 dosages, and at 1 capsule per dosage for the following 3 dosages.

TABLE 3

A Composition For Treating Hand And Wrist Discomfort

| SUBSTANCE [commercial source] | AMOUNT (mg) |
|---|---|
| Baishaoyao [Qualiherb, Cerritos, CA] | 33.3 |
| Fangfeng [Qualiherb, Cerritos, CA] | 33.3 |
| Guizi [Qualiherb, Cerritos, CA] | 50 |
| Honghua [Qualiherb, Cerritos, CA] | 33.3 |
| Chuanxiong [Qualiherb, Cerritos, CA] | 50 |
| Yuanhusuo [Mayway, Oakland, CA] | 50 |
| Dangquiwei [Mayway, Oakland, CA] | 50 |
| Gancao [Qualiherb, Cerritos, CA] | 33.3 |
| Ginger [Qualiherb, Cerritos, CA] | 33.3 |
| Huangqi [Mayway, Oakland, CA] | 1.33 |
| Sangzhi [Qualiherb, Cerritos, CA] | 66.7 |
| Yinyanghuo [Qualiherb, Cerritos, CA] | 33.3 |
| Weilingxian [Mayway, Oakland, CA] | 66.7 |
| Dazao [Mayway, Oakland, CA] | 16.7 |
| Vitamin B-1 (Thiamine) [Acta, Sunnyvale, CA] | 4.2 |
| Vitamin B-2 (Riboflavin) [Acta, Sunnyvale, CA] | 4.2 |
| Vitamin B-3 (Niacin) [Acta, Sunnyvale, CA] | 8.3 |
| Vitamin B-5 (Pantothenic acid) [Acta, Sunnyvale, CA] | 4.2 |
| Vitamin B-6 (pyridoxine) [Acta, Sunnyvale, CA] | 33 |
| Vitamin C (ascorbic acid) [Acta, Sunnyvale, CA] | 100 |
| Vitamin E (D alpha-tocopherol succinate) [Acta, Sunnyvale, CA] | 14.1 |
| Beta-carotene [Acta, Sunnyvale, CA] | 7.5 |
| Zinc gluconate [Acta, Sunnyvale, CA] | 21 |
| Quercetin [Acta, Sunnyvale, CA] | 8.3 |
| Selenium aminoate [Acta, Sunnyvale, CA] | 6.7 |
| Rice flour powder [Acta, Sunnyvale, CA] | 10 |
| Magnesium stearate NT [Acta, Sunnyvale, CA] | 10 |

Prior to administration of the composition(s), the individual was asked to rate the severity of her symptoms on a scale of 0 to 5, 0 being normal condition and 5 being severe pain. Subsequently, the individual was asked to assess her symptoms within 4 hours after each administration of the composition(s). The individual was instructed to assess frequency of pain (e.g., occasional, intermittent, or constant) as a primary criterion for pain severity. If administration occurred at bedtime, symptoms were assessed the following morning.

Results of the study are provided in Table 4.

TABLE 4

Severity of Wrist Pain

| Dosage No. | 0 | 1 | 2 | 3 | 4 | 5 | 6 | 7 | 8 | 9 | 10 | 11 | 12 |
|---|---|---|---|---|---|---|---|---|---|---|---|---|---|
| Bout A (severity) | 4 | 4 | 4 | 4 | 4 | 4 | 4 | 4 | 4 | 4 | 4 | 3 | 3 |
| Bout B (severity) | 4 | 4 | 4 | 4 | 3 | 2 | 1 | 1 | 0.5 | 0 | 0 | 0 | 0 |

The data show a clear and significant enhancement of therapeutic effect when the composition of Example 1 in the instant specification was co-administered with the composition for treating wrist pain.

Example 4

Illustrative Example of Enhancement of Therapeutic Effects of a Composition for Treating Eye Discomfort A randomized, double-blinded and controlled study is performed. Individuals suffering from eye discomfort such as dry eyes are divided into three groups. Individuals in the first group are administered the composition set forth in Table 5. The composition of Table 5 is exemplified as Example 1 of co-pending patent application entitled "Compositions And Methods For Treating Eye Discomfort" (which is hereby incorporated herein by reference in its entirety). Individuals in the second group are administered the composition exemplified in Example 1 of the instant specification. Individuals in the third group are co-administered the compositions administered to the individuals of the first and second group. Preferably, a fourth group is included in which individuals are administered a placebo that does not contain any of the substances found in the compositions administered to the first and second group.

TABLE 5

A Composition For Treating Eye Discomfort

| SUBSTANCE [Commercial source] | AMOUNT (mg) |
|---|---|
| Fuling [Qualiherb, Cerritos, CA] | 16.7 |
| Jueminzi [Qualiherb, Cerritos, CA] | 8.3 |
| Sang ye [Qualiherb, Cerritos, CA] | 33.3 |
| Shanyao [Qualiherb, Cerritos, CA] | 16.7 |
| Shanzhuyu [Mayway, Oakland, CA] | 16.7 |
| Shudihaung [Qualiherb, Cerritos, CA] | 100.0 |
| Bilberry [Acta, Sunnyvale, CA] | 16.7 |
| Danshen [Qualiherb, Cerritos, CA] | 16.7 |
| Gouqizhi [Qualiherb, Cerritos, CA] | 100.0 |
| Juhua [Qualiherb, Cerritos, CA] | 66.7 |
| Baijili [Qualiherb, Cerritos, CA] | 16.7 |
| Beta-carotene [Acta, Sunnyvale, CA] | 22.5 |
| Copper gluconate [Acta, Sunnyvale, CA] | 7.1 |
| Gujincao [Qualiherb, Cerritos, CA] | 8.3 |
| Magnesium stearate NF [Acta, Sunnyvale, CA] | 10.0 |
| Mudanpi [Qualiherb, Cerritos, CA] | 16.7 |
| Rice flour powder [Acta, Sunnyvale, CA] | 8.3 |
| Seleniuum aminoate [Acta, Sunnyvale, CA] | 6.7 |
| Vitamin B-2 (riboflavin) [Acta, Sunnyvale, CA] | 5.0 |
| Vitamin C (ascorbic acid) [Acta, Sunnyvale, CA] | 66.7 |
| Vitamin E (D Alpha-tocopherol succinate) [Acta, Sunnyvale, CA] | 76.0 |
| Zexie [Acta, Sunnyvale, CA] | 16.7 |
| Zinc gluconate [Acta, Sunnyvale, CA] | 57.7 |

Individuals in the first group are daily administered from 1 to 6 capsules of the composition of Table 5. Individuals in the second group are daily administered from 1 to 6 of the capsules of Example 1 of the instant specification. Individuals in the third group are daily administered the combined dosages of the individuals of the first and second group.

At least 20 individuals are tested, randomly assigned in approximately equal number to the various groups. Individuals are evaluated to suffer from a particular eye discomfort symptom, such as dry eyes.

The study is carried out for at least 1 week. During the treatment course, a dosage amount selected from the range of 1 to 6 capsules of each composition is administered to each individual once or multiple times daily, not exceeding 6 capsules of each composition per day. Capsules are administered before or after food-consumption.

A clinical questionnaire is used to evaluate individuals' eye discomfort symptoms. A clinical coordinator and/or physician evaluates the individuals' eye discomfort symptoms and fills out the questionnaire. Evaluations can be performed daily, or more or less frequently depending on statistical or clinical (ability to detect or track symptomatic improvements) need.

Assessment of symptoms is divided into 4 grades: (1) clinical cure, as defined as free of symptoms; (2) significant efficacy, as defined as significantly improved symptoms (e.g., reduction of more than 3 points on any one of discomfort scoring scales); (3) efficacy, as defined as partially improved (e.g. reduction of more than 1 point on any one of discomfort scoring scales); and (4) non-efficacy, as defined as no improvement in symptoms.

The results of the groups are compared to assess any enhanced therapeutic effects due to the co-administration of the composition exemplified in Example 1.

Example 5

Illustrative Example of Enhancement of Therapeutic Effects of a Composition for Treating Wrist Discomfort A randomized, double-blinded and controlled study is performed. Individuals suffering from wrist discomfort such as wrist pain are divided into three groups. Individuals in the first group are administered the composition set forth in Table 3. Individuals in the second group are administered the composition exemplified in Example 1 of the instant specification. Individuals in the third group are co-administered the compositions administered to the individuals of the first and second group. Preferably, a fourth group is included in which individuals are administered a placebo that does not contain any of the substances found in the compositions administered to the first and second group.

Individuals in the first group are daily administered from 1 to 6 capsules of the composition of Table 3. Individuals in the second group are daily administered from 1 to 6 of the capsules of Example 1 of the instant specification. Individuals in the third group are daily administered the combined dosages of the individuals of the first and second group.

At least 20 individuals are tested, randomly assigned in approximately equal number to the various groups. Individuals are evaluated to suffer from a particular wrist discomfort symptom, such as wrist pain.

The study is carried out for at least 1 week. During the treatment course, a dosage amount selected from the range of 1 to 6 capsules of each composition is administered to each individual once or multiple times daily, not exceeding 6 capsules of each composition per day. Capsules are administered before or after food consumption.

A clinical questionnaire is used to evaluate individuals' wrist discomfort symptoms. A clinical coordinator and/or physician evaluates the individuals' wrist discomfort symptoms and fills out the questionnaire. Evaluations can be performed daily, or more or less frequently depending on statistical or clinical (ability to detect or track symptomatic improvements) need.

Assessment of symptoms is divided into 4 grades: (1) clinical cure, as defined as free of symptoms; (2) significant efficacy, as defined as significantly improved symptoms (e.g., reduction of more than 3 points on any one of discomfort scoring scales); (3) efficacy, as defined as partially improved (e.g. reduction of more than 1 point on any one of discomfort scoring scales); and (4) non-efficacy, as defined as no improvement in symptoms.

The results of the groups are compared to assess any enhanced therapeutic effects due to the co-administration of the composition exemplified in Example 1.

Example 6

Illustrative Example of Enhancement of Therapeutic Effects of a Composition for Treating Back and Leg Discomfort A randomized, double-blinded and controlled study is performed. Individuals suffering from back or leg discomfort such as back or leg pain are divided into three groups. Individuals in the first group are administered the composition set forth in Table 6. The composition of Table 6 is exemplified as Example 1 of co-pending patent application entitled "Compositions And Methods For Treating Back And Leg Discomfort" (which is hereby incorporated herein by reference in its entirety). Individuals in the second group are administered the composition exemplified in Example 1 of the instant specification. Individuals in the third group are co-administered the compositions administered to the individuals of the first and second group. Preferably, a fourth group is included in which individuals are administered a placebo that does not contain any of the substances found in the compositions administered to the first and second group.

TABLE 6

A Composition For Treating Back And Leg Discomfort

| SUBSTANCE [commercial source] | AMOUNT (mg) |
| --- | --- |
| Duzhong [Mayway, Oakland, CA] | 33 |
| Huainiuxi [Qualiherb, Cerritos, CA] | 33 |
| Jixueteng [Qualiherb, Cerritos, CA] | 117 |
| Qiannianjian [Qualiherb, Cerritos, CA] | 33 |
| Rougui [Qualiherb, Cerritos, CA] | 50 |
| Xiquancao [Qualiherb, Cerritos, CA] | 133 |
| Jinyingzi [Mayway, Oakland, CA] | 33 |
| Tougucao [Qualiherb, Cerritos, CA] | 33 |
| Duhuo [Qualiherb, Cerritos, CA] | 100 |
| Weilingxian [Mayway, Oakland, CA] | 67 |
| Shenjincao [Qualiherb, Cerritos, CA] | 17 |
| Vitamin B-1 [Acta, Sunnyvale, CA] | 5 |
| Vitamin B-2 [Acta, Sunnyvale, CA] | 5 |
| Vitamin B-6 [Acta, Sunnyvale, CA] | 15 |
| Vitamin B-12 [Acta, Sunnyvale, CA] | 0.0125 |
| Vitamin C (ascorbic acid) [Acta, Sunnyvale, CA] | 30 |
| Vitamin E (D Alpha-Tocopherol) [Acta, Sunnyvale, CA] | 21.19 |
| Devil's Claw [Acta, Sunnyvale, CA] | 10 |
| Black cohosh [Acta, Sunnyvale, CA] | 10 |
| Selenium [Acta, Sunnyvale, CA) | 20 |

Individuals in the first group are daily administered from 1 to 6 capsules of the composition of Table 6. Individuals in the second group are daily administered from 1 to 6 of the capsules of Example 1 of the instant specification. Individuals in the third group are daily administered the combined dosages of the individuals of the first and second group.

At least 20 individuals are tested, randomly assigned in approximately equal number to the various groups. Individuals are evaluated to suffer from a particular back or leg discomfort symptom, such as back or leg pain.

The study is carried out for at least 1 week. During the treatment course, a dosage amount selected from the range of 1 to 6 capsules of each composition is administered to each individual once or multiple times daily, not exceeding 6 capsules of each composition per day. Capsules are administered before or after food consumption.

A clinical questionnaire is used to evaluate individuals' back or leg discomfort symptoms. A clinical coordinator and/or physician evaluates the individuals' back or leg discomfort symptoms and fills out the questionnaire. Evaluations can be performed daily, or more or less frequently depending on statistical or clinical (ability to detect or track symptomatic improvements) need.

Assessment of symptoms is divided into 4 grades: (1) clinical cure, as defined as free of symptoms; (2) significant efficacy, as defined as significantly improved symptoms (e.g., reduction of more than 3 points on any one of discomfort scoring scales); (3) efficacy, as defined as partially improved (e.g. reduction of more than 1 point on any one of discomfort scoring scales); and (4) non-efficacy, as defined as no improvement in symptoms.

The results of the groups are compared to assess any enhanced therapeutic effects due to the co-administration of the composition exemplified in Example 1.

Example 7

Illustrative Example of Enhancement of Therapeutic Effects of a Composition for Treating Neck and Shoulder Discomfort A randomized, double-blinded and controlled study is performed. Individuals suffering from neck or shoulder discomfort such as neck or shoulder pain are divided into three groups. Individuals in the first group are administered the composition of Table. 2. Individuals in the second group are administered the composition exemplified in Example 1 of the instant specification. Individuals in the third group are co-administered the compositions administered to the individuals of the first and second group. Preferably, a fourth group is included in which individuals are administered a placebo that does not contain any of the substances found in the compositions administered to the first and second group.

Individuals in the first group are daily administered from 1 to 6 capsules of the composition of Table 2. Individuals in the second group are daily administered from 1 to 6 of the capsules of Example 1 of the instant specification. Individuals in the third group are daily administered the combined dosages of the individuals of the first and second group.

At least 20 individuals are tested, randomly assigned in approximately equal number to the various groups. Individuals are evaluated to suffer from a particular neck or shoulder discomfort symptom, such as neck or shoulder pain.

The study is carried out for at least 1 week. During the treatment course, a dosage amount selected from the range of 1 to 6 capsules of each composition is administered to each individual once or multiple times daily, not exceeding 6 capsules of each composition per day. Capsules are administered before or after food consumption.

A clinical questionnaire is used to evaluate individuals' neck or shoulder discomfort symptoms. A clinical coordinator and/or physician evaluates the individuals' neck or shoulder discomfort symptoms and fills out the questionnaire. Evaluations can be performed daily, or more or less frequently depending on statistical or clinical (ability to detect or track symptomatic improvements) need.

Assessment of symptoms is divided into 4 grades: (1) clinical cure, as defined as free of symptoms; (2) significant efficacy, as defined as significantly improved symptoms (e.g., reduction of more than 3 points on any one of discomfort scoring scales); (3) efficacy, as defined as partially improved (e.g. reduction of more than 1 point on any one of discomfort scoring scales); and (4) non-efficacy, as defined as no improvement in symptoms.

The results of the groups are compared to assess any enhanced therapeutic effects due to the co-administration of the composition exemplified in Example 1.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A first composition for enhancing the therapeutic effects of a second composition, said first composition comprising *xuejie, yanhusuo, baishaoyao, shanqi, gancao*, white willow bark, black cohosh root, L-carnitine, vitamin E and vitamin C.

\* \* \* \* \*

UNITED STATES PATENT AND TRADEMARK OFFICE
CERTIFICATE OF CORRECTION

PATENT NO. : 6,383,524 B2
DATED : May 7, 2002
INVENTOR(S) : Yuanjin Tao

It is certified that error appears in the above-identified patent and that said Letters Patent is hereby corrected as shown below:

Column 20,
Line 4, please replace "L-camitine" with -- L-carnitine --;

Signed and Sealed this

Seventeenth Day of February, 2004

JON W. DUDAS
*Acting Director of the United States Patent and Trademark Office*